United States Patent [19]

Chamoun

[11] Patent Number: 4,907,597
[45] Date of Patent: Mar. 13, 1990

[54] CEREBRAL BIOPOTENTIAL ANALYSIS SYSTEM AND METHOD

[75] Inventor: Nassib G. Chamoun, Roxbury, Mass.

[73] Assignee: Biometrak Corporation, Cambridge, Mass.

[21] Appl. No.: 107,357

[22] Filed: Oct. 9, 1987

[51] Int. Cl.$^4$ .............................................. A61B 5/04
[52] U.S. Cl. ................................................... 128/731
[58] Field of Search ........................ 128/731, 733, 734; 364/726, 413.05

[56] References Cited

U.S. PATENT DOCUMENTS

| 4,557,270 | 12/1985 | John | 128/731 |
| 4,753,246 | 6/1988 | Freeman | 128/731 |

OTHER PUBLICATIONS

Withington, P. S., Morton, J., Arnold, R., Sebel, P. S., and Moberg, R., Assessment of Power Spectral Edge for Monitoring Depth of Anesthesia Using Low Methohexitone Infusion, Int-J-Clin-Monit-Computing, 3(2): pp. 117-122 (1986).
Levy, W. J., Intraoperative EEG Patterns: Implications for EEG Monitoring, Anesthesiology, 60(5): pp. 430-434 (1984).
Pichlmayr, I., and Lips, U., EEG Monitoring in Anesthesiology and Intensive Care., Neuropsychobiology, 10(4): pp. 239-248 (1983).
Baker, A. B., and Roxburgh, A. J., Computerised EEG Monitoring for Carotid Endarterectomy, Anaesth-Intensive Care, 14(1): pp. 32-36 (1986).
Brillinger, D. R., An Introduction to Polyspectra, Annals of Mathematical Statistics 36:1351-74 (1965).
Russ, W., Kling, D., Krumholz, W., Fraedrich, G., and Hempelmann, G., [Experience with a New EEG Spectral Analyzer in Carotid Surgery] Erfahrungen mit einem neuen EEG-Spektralanalysator in der Karotischirurgie, Anaesthetist 34(2): pp. 85-90 (1985).
Rampil, I. J., Holzer, J. A., Quest, D. O., Rosenbaum, S. H., and Correll J. W., Prognostic Value of Computerized EEG Analysis During Carotic Endarterectomy, Anesthesia Analgesia 62:186-92 (1983).
Huber, P. J., B. Kleiner, T. Gasser and G. Dumermuth, Statistical Method for Investigating Phase Relations in Stationary Stochastic Processes, IEEE Trans. Aud. & Electroacou. AU-19/1:78-86 (1971).
Tryon, P. V., The Bispectrum and Higher-Order Spectra: A bibliography, US NBS (Tech Note 1036) (1981).
Nikias, C. L., and Raghuveer, M. R., Bispectrum estimation: A Digital Signal Processing Framework, Proc. IEEE, 75, 7:869-91 (1987).
Susumu, T. and Osamu, T., Analysis of Wave Shapes of (List continued on next page.)

Primary Examiner—Francis Jaworski
Assistant Examiner—George Manuel

[57] ABSTRACT

Disclosed is a biopotential analysis system and method of the present invention for determining, in a noninvasive manner, cerebral electrical properties. A suitable electrode and amplifier system is used to obtain biopotentials from the region of interest. Surface electroencephalographic signals are then digitized and transmitted over a serial RS232C line to a host computer where a two minute long signal is divided into 30 consecutive four second intervals. A fast Fourier transform (FFT) is then performed on every interval, and the resulting fast Fourier transforms are then used to produce bispectral complex triple product and bispectral real triple product arrays for that interval. The complex triple product arrays of all intervals are added together, and the real triple product arrays of all intervals are also added together. Each element in the final complex array and final real array is then divided by 30 (the number of intervals) to produce an average complex triple product array and an average real triple product array. The magnitude squared of each element in the complex triple product array is divided by the corresponding element in the real triple product array to form the bicoherence array. The bicoherence array is displayed on a video terminal or plotted, and is used as a figure of merit for the assessment of cerebral electrical function.

28 Claims, 8 Drawing Sheets

OTHER PUBLICATIONS

Alpha Waves on EEG by Means of the Bispectrum, (1973).

Kleiner, B., Huber, P. J., and Dumermuth, G., Analysis of the Interelations between Frequency Bands of the EEG by Means of the Bispectrum, Electroencephalogr. Neurophysiol. 27(7): 693–694 (1969).

Dumermuth, G., Huber, P. J., Kleiner, B., and Gasser, T., Analysis of the Interrelations between Frequency Bands of the EEG by Means of the Bispectrum, A preliminary study, Electroencephalogr. Clin. Neurophysiol. 31(2):137–148 (1971).

Barnett, T. P., Johnson, L. C., Naitoh, P., Hicks, N. and Nute, C., Bispectrum Analysis of Electroencephalogram Signals During Waking and Sleeping, Science 172:402–401 (1971).

Raghuveer, M. R. and Nikias, C. L., Bispectrum Estimation: A Parametric Approach, IEEE Trans. on Acoustics, Speech & Signal Processing, 33:1213–1230 (1985).

Volavka, J., Matousek, M., Feldstein, S. et al., The Reliability of Electroencephalography Assessment., Electroencephalography and Electromyography, 4: 123 (1973).

Eichhorn, J. H., Cooper, J. B., Cullen, D. J., Ward, M. R., Philip, J. H., and Seeman, R. G., Standards for Patient Monitoring During Anesthesia at Harvard Medical School, JAMA, 256(8): pp. 1017–1020 (1986).

Jasper, H. H., The Ten-Twenty Electrode System of the International Federation in Electroencephalography and Clinical Neurophysiology, EEG Journal, 10:371–375 (1985).

Haykin, S., Adaptive Filter Theory, Prentice-Hall, Englewood Cliffs, N.J. (1986).

Fig. 5
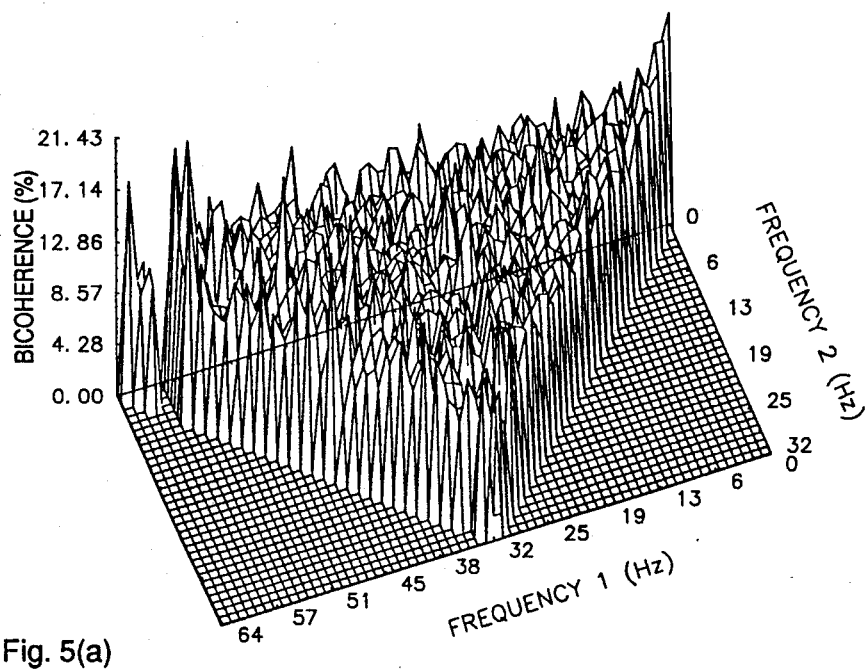
Fig. 5(a)
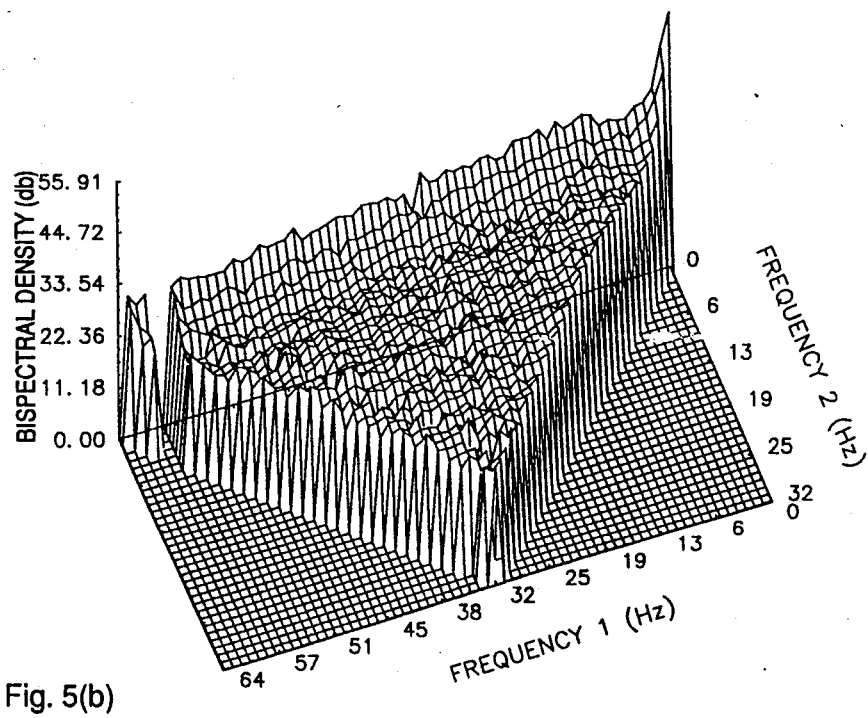
Fig. 5(b)

CEREBRAL BIOPOTENTIAL ANALYSIS SYSTEM AND METHOD

BACKGROUND OF THE INVENTION

The present invention relates to a biopotential analysis system and method, and more particularly to a computer-based biopotential analysis system for determining, in a noninvasive manner, cerebral electrical properties.

Despite a considerable expenditure of time and effort, no approach for permitting quantitative, noninvasive assessments of cerebral electrical activity has been developed. A number of known devices are capable of providing a qualitative tracking of cerebral activity. Techniques such as the conventional EEG are restricted to analyses in the time domain. A more recent approach utilizes quantification of the frequency content of the EEG signal, as determined by the Fourier transform of the second order correlation function (better known as the power spectrum), but this technique has proven to be useful in only a limited number of situations.

The discharge of thousands of electrically active cells in the brain, organized in larger, interacting neural centers contributes to the formation of an extremely complicated, but well coordinated electrical signal. Embedded in that signal is information regarding frequency content, non-linearities, and phase relationships, all arising from the complex cerebral dynamics that take place. Because of the complexity of the EEG signal, conventional time and frequency modes of analysis are not particularly productive. The EEG is highly non-linear, and its intrinsic phase relationships must carry a great deal of information regarding cerebral function. Unfortunately, the power spectrum suppresses information regarding non-linearities and phase relationships and thus is of limited utility in extracting information available in the EEG.

The Fourier transform of the third order auto-correlation function, or bispectrum, is an analytic process that quantifies non-linearities and phase relationships intrinsic to any waveform. Although the application of bispectral analysis to EEG signals can be found in the prior art, it was only used as a test for demonstration purposes. The only known application was by T. P. Barnett and is described in Science 172:41-402 (1971), where bispectral analysis was applied to the EEG during various phases of sleep.

It is therefore a principal object of the present invention to provide a noninvasive system and method for diagnosing cerebral irregularities.

Another object of the present invention is to provide a system and method for noninvasively obtaining an intraoperative detection and quantification of cerebral ischemia.

A still further object of the present invention is to provide an apparatus and method for quantifying the adequacy of oxygenation of the critical region probed by a particular EEG lead.

A further object of the present invention is to provide a system and method for noninvasively quantifying the depth of anesthesia.

Yet another object of the present invention is to provide an apparatus and method for noninvasively quantifying the degree of intoxication.

SUMMARY OF THE INVENTION

The biopotential analysis system and method of the present invention determines, in a noninvasive manner, cerebral electrical properties. A suitable electrode and amplifier system is used to obtain biopotentials from the region of interest. Surface electroencephalographic signals are then digitized and transmitted over a serial RS232C line to a host computer where a two minute long signal is divided into 30 consecutive four second intervals. A fast Fourier transform (FFT) is then performed on every interval, and the resulting fast Fourier transforms are then used to produce bispectral complex triple product and bispectral real triple product arrays for that interval. The complex triple product arrays of all intervals are added together, and the real triple product arrays of all intervals are also added together. Each element in the final complex array and final real array is then divided by 30 (the number of intervals) to produce an average complex triple product array and an average real triple product array. The magnitude squared of each element in the complex triple product array is divided by the corresponding element in the real triple product array to form the bicoherence array. The bicoherence array is displayed on a video terminal or plotted, and is used as a figure of merit for the assessment of cerebral electrical function.

Since the bispectral process involves an evaluation of the relational components of the fundamental constituents of any signal without regard to the absolute magnitudes of the signals, the bispectral decomposition of the EEG signal yields a unique quantitative description of cerebral electrical behavior. Deviation from normal electrical activity patterns in the brain (whether due to ischemia or anesthesia) will lead to an alteration in the "fine fingerprint" embedded in the structure of the surface EEG signal. Since bispectral analysis is able to extract a quantitative fingerprint inherent in any signal, it provides a unique quantitative index of the influence of ischemia or anesthetic drugs on electrical properties and function of the brain.

These and other objects and features of the present invention will be more fully understood from the following detailed description which should be read in light of the accompanying drawings in which corresponding reference numerals refer to corresponding parts throughout the several views.

BRIEF DESCRIPTION OF THE DRAWINGS

FIG. 5(a) is a diagram of a sample simulated three-dimensional plot of a bicoherence array and FIG. 5(b) is a diagram of a sample simulated three-dimensional plot of a bispectral density array.

DETAILED DESCRIPTION OF THE PREFERRED EMBODIMENTS

Figure 1:
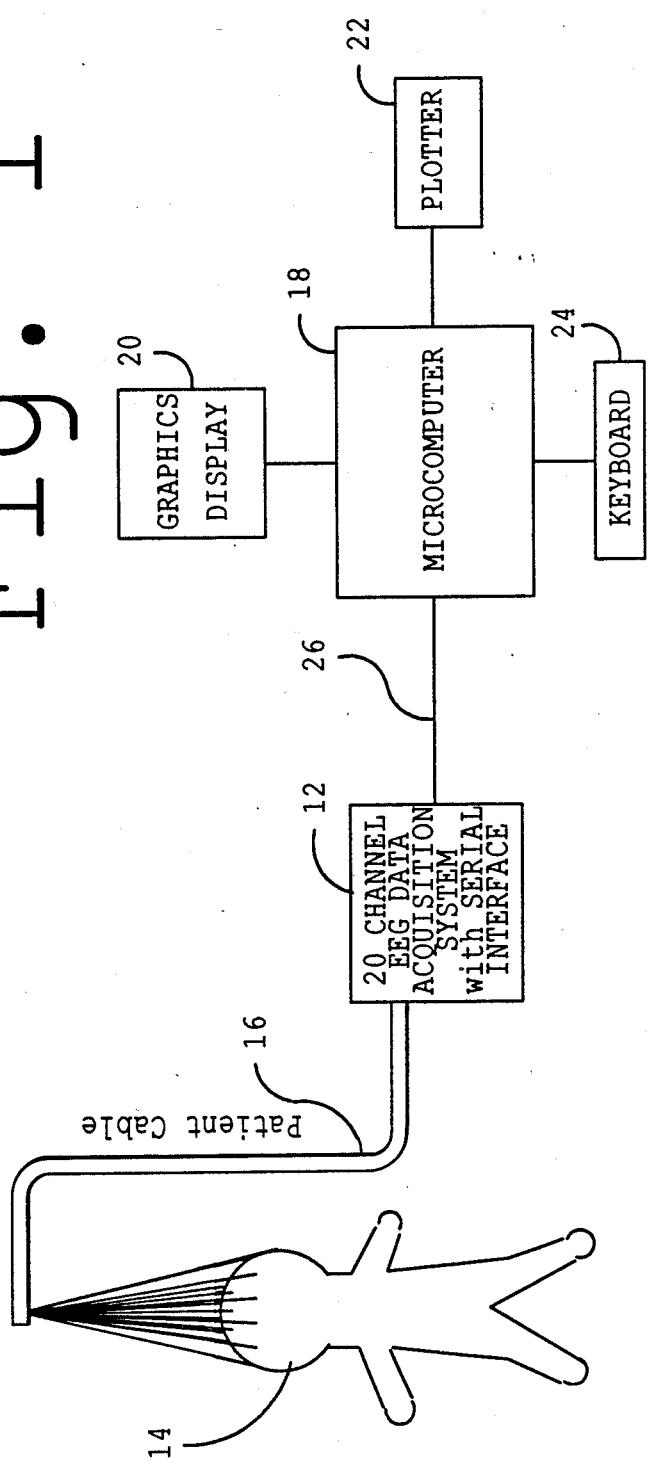
FIG. 1 is a schematic view of the system Of the present invention for acquiring, calculating and displaying the EEG bispectrum.

Referring to FIG. 1 the bispectral analysis system of the present invention includes a 20 channel EEG data acquisition system 12 which includes a serial interface. The EEG leads are connected to the patient 14, and the signals picked up by the leads are transmitted over a patient cable 16 to the EEG data acquisition system 12. The data acquisition system 12 amplifies and digitizes the EEG waveforms and sends the digitized data to the microcomputer 18 via a serial port for analysis. In addition, the serial line can be used to download instructions to the data acquisition unit 12. The microcomputer 18 analyses the serial data stream and calculates the bispectrum, which is displayed on the graphic display 20. Hard copy output of the bispectral waveforms is also available on plotter 22 which is connected to the microcomputer 18. Interaction between the operator and the acquisition analysis programs is provided by means of a keyboard 24 with feedback on the graphics display 20.

Figure 2:
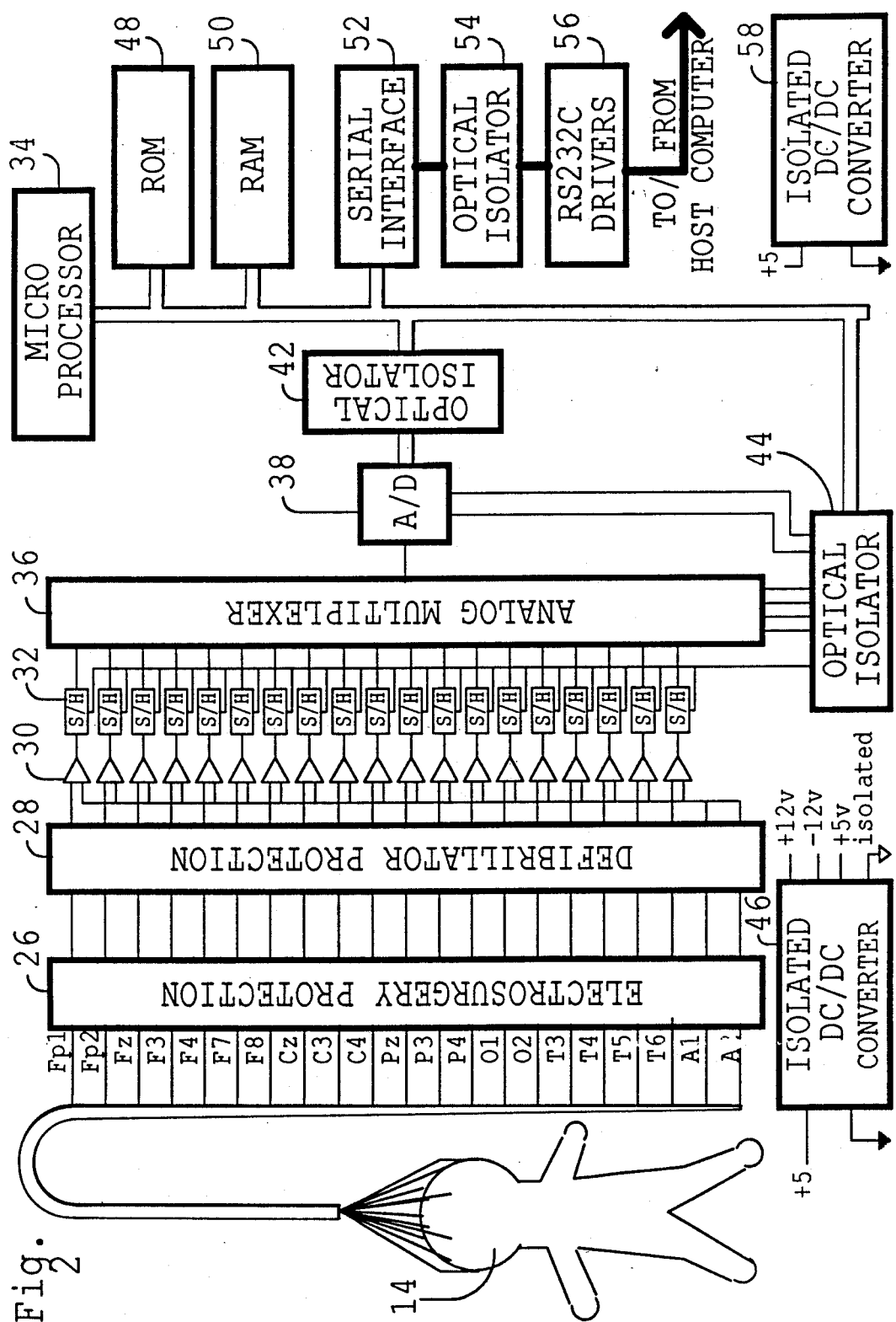
FIG. 2 is a schematic view of a 20 channel EEG data acquisition system including a serial interface utilized in the system of FIG. 1.

The 20 channel data acquisition system 12 is shown in greater detail in FIG. 2. The EEG surface potential detected by a surface electrode mounted on the patient 14 passes through an electrosurgery protection circuit 26 and a defibrillator protection circuit 28 before being passed on to the amplifier circuitry 30. The electrosurgery protection circuit 26 includes a radio frequency (rf) filter, which limits the rf current through the patient leads and thus protects the patient 14 from rf burns and protects the amplifiers 30 from damage. The defibrillator protection circuit 28 limits the voltage to the amplifiers 30 to a safe level when a defibrillator is applied to the patient and discharged. The defibrillator protection circuit 28 also limits the current through patient leads during a defibrillator discharge.

The output of all 20 channels of the amplifier is fed to 20 sample and hold circuits 32 which are under program control of microprocessor 34. The output of the sample and hold circuits 32 is multiplexed by multiplexer 36 and digitized by a 16 bit analog-to-digital converter 38 at a rate of 128/sec thus providing temporal resolution of better than 16 msec. The output of the analog-to-digital converter 38 is optically coupled to data bus 40 by optical isolator 42. All control lines to the sample and hold circuits 32, the multiplexer 36 and the analog-to-digital convertor 38 are also optically isolated by optical isolator 44. All DC power lines going to the amplifiers 30, sample and hold circuits 32, multiplexer 36 and analog-to-digital convertor 38 are also isolated from the AC power line with a DC/DC convertor 46 in order to provide complete patient isolation from ground.

The basic instructions for controlling operation of the microprocessor 34 are stored in a read-only memory (ROM 48). The random access memory (RAM 50) is used as a buffer memory for data and a portion of the RAM 50 can also be used as program memory when a control program is being downloaded from the microcomputer 18. The serial interface 52 operates under the control of the microprocessor 34 and a serial interface 52 is optically coupled with optical isolators 54 to RS232C drivers 56 to provide a serial interface between the 20 channel data acquisition system 12 and any standard RS232 serial port on any computer. The serial lines are isolated by optical isolators 54 and DC/DC convertor 58 to provide increased patient safety and to protect the host computer 18 from any transients.

Figure 3:
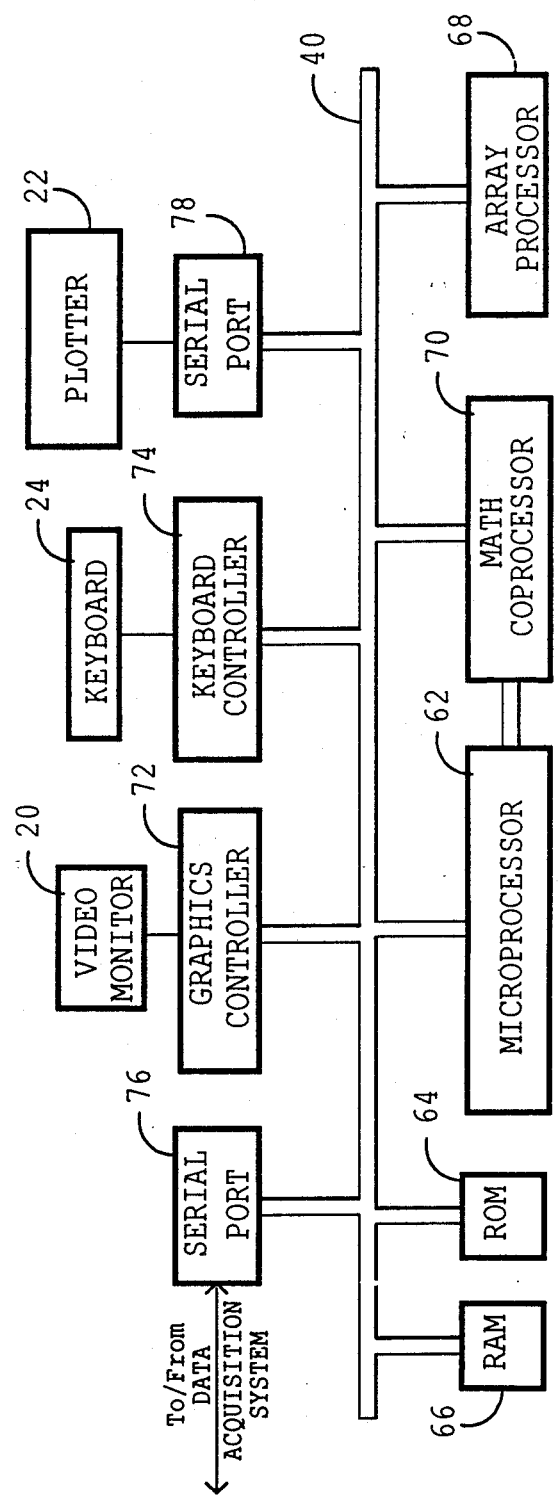
FIG. 3 is a schematic view of the microcomputer used to calculate and display the EEG bispectrum in the system of FIG. 1.
Figure 4:
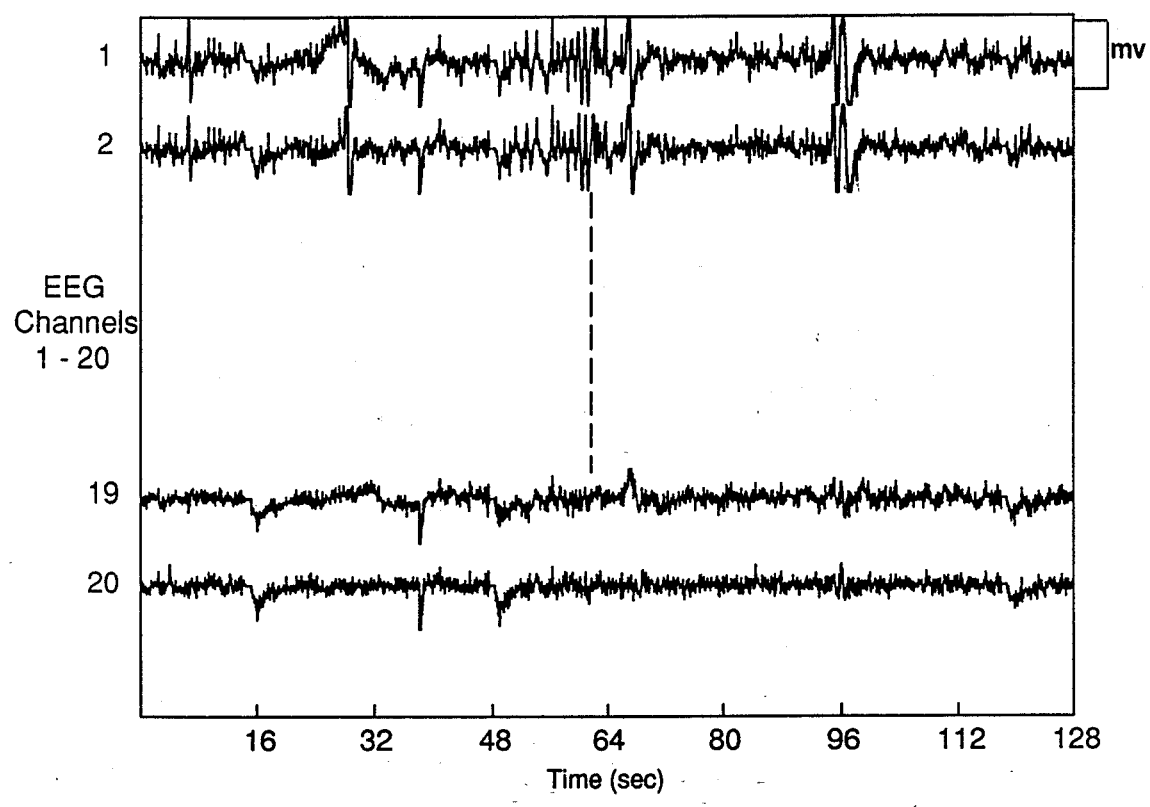
FIG. 4 is a diagram showing sample non-calibrated EEG signals.

The host or microcomputer 18 of FIG. 1 is shown in greater detail in FIG. 3. The entire microcomputer system runs under control of the microprocessor 62 with the program memory for the microprocessor 62 being stored in ROM 64. The RAM 66 is used for storage of intermediate data. In a preferred embodiment, the microcomputer 18 will contain an array processor 68 on which complex arithmetic calculations can be performed on entire arrays of data simultaneously. The preferred embodiment also includes a math coprocessor 70 which is connected directly to microprocessor 62. The math coprocessor 70 is used for scalar and graphic calculations whereas the array processor 68 is used to calculate the bispectrum and other data vectors.

A graphics controller 72 operating under program control of the microprocessor 62 drives a video monitor 20. A keyboard controller 74 interfaces directly with the operator's keyboard 24. Operator control of the entire acquisition, analysis and display procedure is controlled by the keyboard 24 with feedback on the video monitor 20. One serial port 76 is provided to interface with the 20 channel data acquisition system 12. Port 76 can be used to send control data to the system (e.g., start acquisition) and to receive EEG data from the system, as well as to download program data to the system. Another serial port 78 is provided to drive plotter 22 for hard copy output of bispectrum data.

Figure 6:
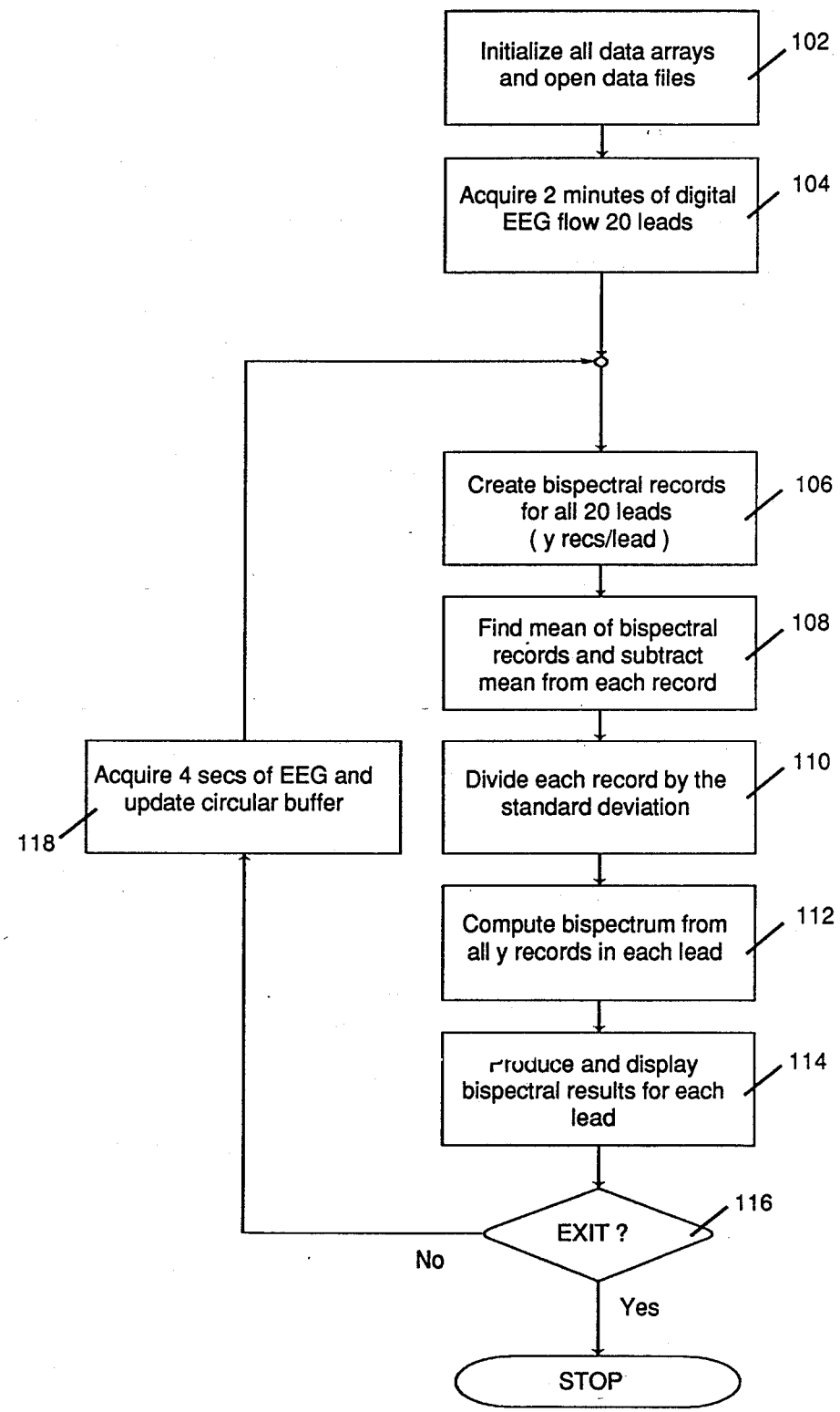
FIG. 6 is a flow chart of the operation used by the microcomputer of FIG. 3 to perform bispectral analysis on electroencephalographic signals intraoperatively.

Referring now to FIG. 6, the operation of the system and method of the present invention will now be described in detail. As mentioned above, the system and method of the present invention computes and determines the bispectral properties of the EEG signals from a preselected number of leads (20 in the described embodiment) with the result being the quantification of cerebral electrical properties. In step 102, the data arrays used to store the digitized EEG, the thirty 4-second records, and the bispectral data of each lead are initialized. The data files required for final storage or comparison with existing pre-anesthesia bispectral density and bicoherence arrays are also opened in the initializing step 102. In step 104, the system begins a two minute acquisition of raw electroencephalographic data from the front end through a general purpose RS232C communication port using a standard protocol such as Kermit. The 120 seconds of digital EEG from each lead are divided into thirty 4-second records to be used for bispectral analysis in step 106. The mean of the samples in each record is subtracted from each sample in that record in step 108, and the sample is then divided by the standard deviation in step 110. This has the effect of normalizing the energy to 1, thereby making this process completely independent of the absolute spectral density at any frequency band.

The bispectrum for each lead is computed using the 30 records of that lead, and this process of computing the bispectrum will be described below with reference to FIG. 7. Finally, after the bispectrum is computed in step 112, the bispectral results relating to cerebral electrical function intraoperatively are produced in a manner described below with reference to FIG. 8. In step 114, the system produces and displays the bispectral results for each lead, and in step 116 the system tests if processing has been completed, and if it has not been, an additional 4 seconds of EEG data are fetched in step 118. A circular buffer mechanism used for storing the first 4-second record for each lead, for moving all records up one record and for storing the latest 4 seconds of data acquired in the location of the 30th record is updated in step 118. Steps 106 through 116 are repeated until readings are no longer required.

Figure 7:
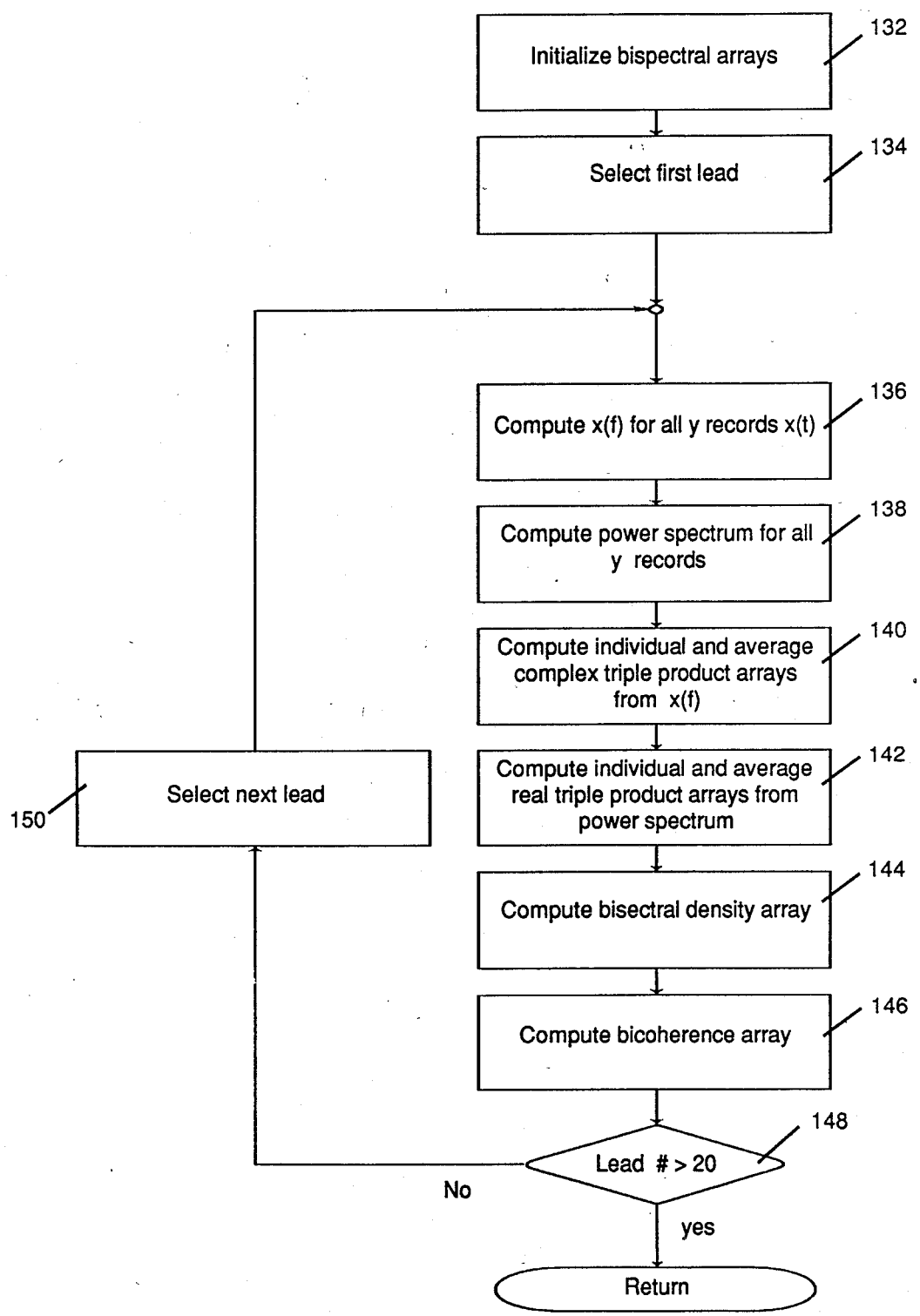
FIG. 7 is a flow chart of the bispectral processing performed by the microcomputer system of FIG. 3.

Referring now to FIG. 7, the method of producing for each lead, the Fourier transform of the third order correlation function which is also referred to as the bispectrum is set out in detail. The arrays which will store the bispectral density results as well as the arrays which will store the bicoherence results are initialized in step 132. In step 134 the first lead is selected for processing. The fast Fourier transform $X_i(f)$ of each record of the 30 selected records for that lead, is computed using a standard IEEE library routine or any other publicly available routine in step 136. In Step 138 the power spectrum $P_i(f)$ of each record of the thirty selected records for that lead is computed by squaring the magnitude of each element of the Fourier transform $X_i(f)$. The average complex triple product is computed by adding all of the individual complex triple products from each record in that lead in Step 140 utilizing the following equations where $bc_i(f_1,f_2)$ is an individual complex triple product and $BC(f_1,f_2)$ is the average complex triple product:

$$bc_i(f_1,f_2) = X_i(f_1) * X_i(f_2) * \overline{X_i(f_1+f_2)}$$

where $f_1$, and $f_2$ are any frequency location in $X(f)$ such that:

$$f_1 + f_2 \leq N/2$$

$$0 \leq f_2 \leq f_1$$

where N=512 (4 secs * 128 samples in a preferred embodiment).

$$BC(f_1,f_2) = 1/30 \left[ \sum_{i=1}^{30} bc_i(f_1,f_2) \right]$$

The average real triple product is computed by adding all of the individual real triple products of each record in that lead in step 142 using the following equations where $br_i(f_1,f_2)$ is an individual real triple product and $BR(f_1,f_2)$ is the average real triple product:

$$br_i(f_1,f_2) = P_i(f_1) * P_i(f_2) * P_i(f_1 + f_2)$$
$$f_1 + f_2 \leq N/2$$

$$BR(f_1,f_2) = 1/30 \left[ \sum_{i=1}^{30} br_i(f_1,f_2) \right]$$

In step 144 the bispectral density array for each lead is computed using the following equation:

$$BD(f_1,f_2) = |BC(f_1,f_2)|^2$$

In step 146 the system computes the bicoherence array $R^2(f_1,f_2)$ for each lead using the following equation:

$$R^2(f_1,f_2) = BD(f_1,f_2)/BR(f_1,f_2)$$

$$0 \leq R^2 \leq 1$$

After testing in step 148 to make sure that all 20 leads have not been processed, the system then selects the next lead in step 150 and steps 136 through 148 are repeated until all of the leads have been processed.

Figure 8:
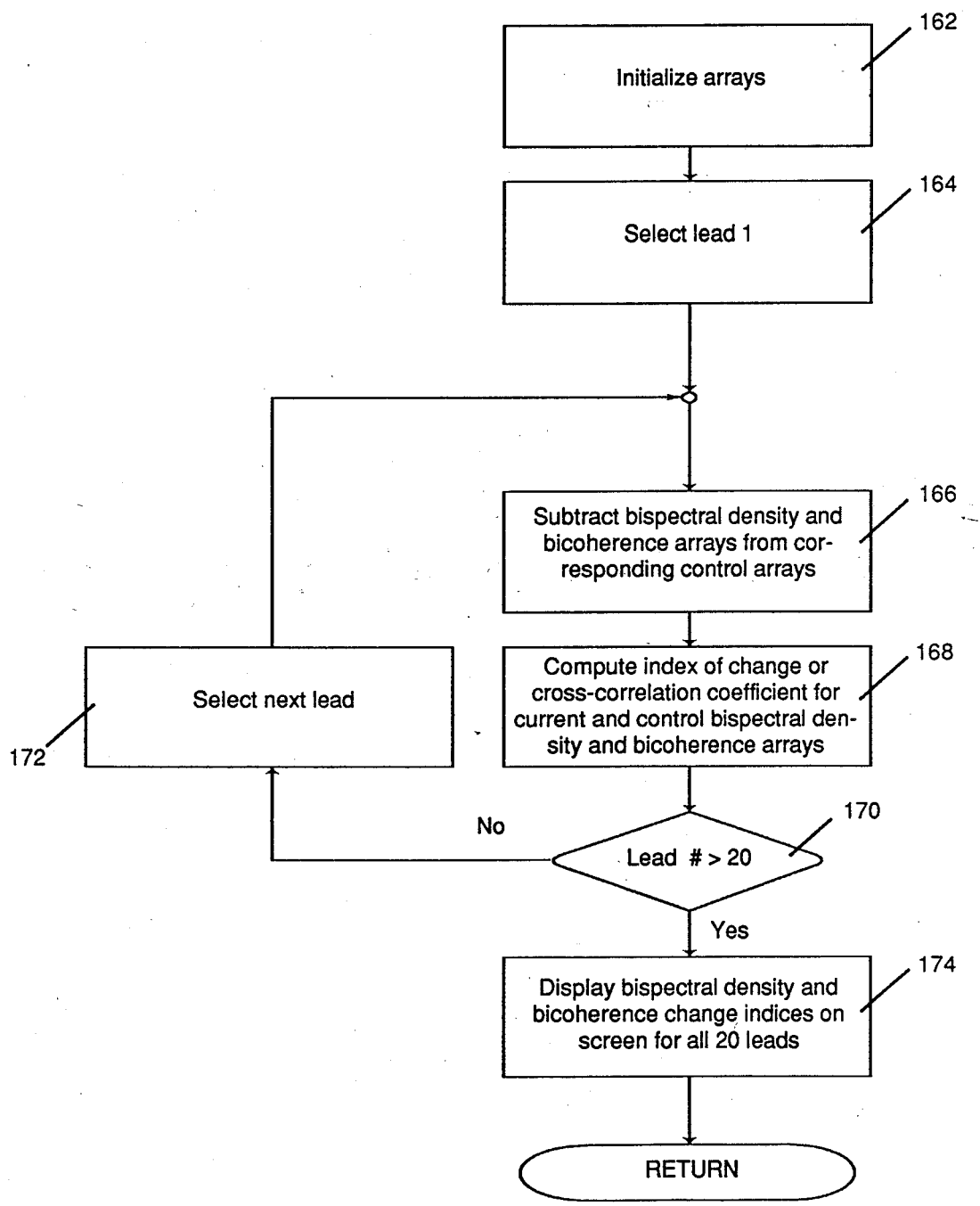
FIG. 8 is a flow chart of the data analysis used to update bispectral changes every four seconds in the course of an operation utilized by the microcomputer system of FIG. 3.

Referring now to FIG. 8, the operation of the system for producing bispectral results relating to cerebral electrical function intraoperatively is shown in greater detail. In step 162 the data arrays used for the analysis of bispectral changes in each lead are initialized. In step 164 the system starts with the first lead in step 164, and subtracts the current bispectral density and current bicoherence arrays from the corresponding control arrays in step 166. The control arrays may be either bispectral density and bicoherence arrays determined from the subject being analyzed prior to the start of the procedure or bispectral density and bicoherence arrays determined from a large population of normal individuals. In step 168 all elements in the bispectral density difference array are added to create the bispectral density change index, and all elements in the bicoherence difference array are added to create the bicoherence change index, for the particular lead. In addition, a two dimensional cross-correlation between the control bispectral density and/or bicoherence arrays (or any subsection thereof) and the current bispectral density and bicoherence arrays may be performed to generate a cross-correlation coefficient representing the distortion and/or deviation from the control bispectral structures.

Then after testing, in step 170, to determine if all of the leads have been processed, the next lead is selected in step 172 and steps 166 through 170 are repeated until all of the leads have been processed. The bispectral density change indexes and/or cross-correlation coefficient, and/or the bicoherence change indexes and/or cross-correlation coefficient for all 20 leads or any subset thereof are displayed simultaneously on the screen in step 174 for evaluation by an operator. The result are then interpreted.

In operation, control bispectral density and bicoherence arrays are produced for each lead, prior to the induction of anesthesia. During the induction of anesthesia and throughout the surgical procedure and the recovery period, the following real time tracking steps are followed with updates every four seconds:

(a) A bispectral density array and a bicoherence array are produced for each lead;

(b) The bispectral density array of each lead is subtracted from the preanesthesia control bispectral density array of that lead;

(c) An index is computed for each lead, representing the sum of all of the absolute values of the changes in each element in the bispectral density array;

(d) The bispectral density array is correlated with a control bispectral density array (or any subsection thereof) and a cross-correlation coefficient is produced.

(e) The bicoherence array of each lead is subtracted from the preanesthesia control bicoherence array of that lead;

(f) An index is computed for each lead, representing the sum of all of the absolute values of the changes in each element in the bicoherence array;

(g) The bicoherence array is correlated with a control bicoherence array (or any subsection thereof) and a cross-correlation coefficient is produced.

(h) The indexes of the changes in the values and/or the cross-correlation coefficient of the bispectral density array, and/or the index of the changes in the values and the cross-correlation coefficient of the bicoherence array for each lead (or any subset thereof) are displayed on a grid. The grid has 20 square areas representative of the location of each lead on the surface of the skull. Each square area will contain both the spectral density index and the bicoherence index and these numbers will be updated every four seconds.

The values of the indexes and the cross-correlation coefficient of each lead are indicative of the depth of anesthesia and its effects on that particular region of the brain. The indexes will increase gradually for all leads during the induction of anesthesia and will reach a maximum after the administered anesthetic dose takes full effect. The indexes will plateau at a level close to the maximum reached during the induction of anesthesia. On the other hand, the cross-correlation coefficient for all leads will decrease during induction of anasthesia and will plateau at a level close to the minimum reached during the induction of anesthesia. The indexes will decline while the cross-correlation coefficient increases as the effect of the anesthetic wears off. If the indexes of any of the leads do increase beyond the maximum reached at the induction of the anesthesia, this increase is indicative of ischemia in the region represented by the lead and appropriate measures should be instituted by the physician. If the cross-correlation coefficient of any of the leads decreases beyond the minimum reached at the induction of the anesthesia, this decrease is indicative of ischemia in the region represented by the lead and appropriate measures should be instituted by the physician.

The system and method of the present invention may be used to process EEG data to serve several other functions as well. For example, in addition to quantifying the depth of anesthesia based on the bispectral analysis of EEG signals, the degree of intoxication due to alcohol or a wide variety of CNS active drugs can also be quantified. The system and method may also be used to quantify the adequacy of oxygenation of the cortical region probed by a particular EEG lead based on bispectral analysis of the signals from that lead. In addition, bispectral parameters may be mapped over the entire cortex by integrating information from all leads.

Finally, while the system and method of the present invention described above are intended to be used primarily in an intraoperative setting, they may also be used for emergency room diagnoses of transient cerebral ischemic attacks and evolving strokes. They may also be used to detect subclinical, asymptomatic impairment of cerebral circulation and may allow the early detection of high-risk patients.

Although bispectral analysis has been applied to the EEG signal, as was discussed above, it has never been used diagnostically for the quantification of the depth of anesthesia or the detection and quantification of cerebral ischemia intraoperatively. Specifically, the system and method of the present invention examines the bicoherences across all frequency pairs, and uses the summed degree of changes in bicoherence and/or bispectral density, and/or the cross-correlation coefficient (between control and current arrays) as an index of physiological perturbation. This allows the quantitative gauging of the disturbances in the cerebral function, whether due to anesthesia, intoxicants or ischemia. The system and method further utilize bicoherences calculated for each lead to create a 2-D map of bicoherences over the cortex. These maps can be generated for any frequency space of interest. By examining a bicoherence map of the relevant frequencies the system and method allow the localization of ischemia and infarct.

While the foregoing invention has been described with reference to its preferred embodiments, various alterations and modifications will occur to those skilled in the art. All such alterations and modifications are intended to fall within the scope of the appended claims.

What is claimed is:

1. A method of noninvasively detecting cerebral irregularities that effect cerebral electrical activity, said method comprising the steps of:

acquiring electroencephalographic signals from a surface of a region of the head of a subject being analyzed through a surface electrode;

dividing said acquired signals into segments and representing said segments as data records;

computing bispectral values for all data records of said acquired signals;

utilizing said bispectral values to generate single number indices to quantify a contribution to overall cerebral electrophysiologic stability provided by the region to which said surface electrode is connected.

2. The method of noninvasively detecting cerebral irregularities of claim 1 wherein said step of acquiring electroencephalographic signals comprises the step of:

placing a surface electrode on a region of the head of said subject being analyzed and detecting signals relating to cerebral activity in the region where the electrode is placed;

amplifying signals detected by said surface electrodes;

digitizing said amplified signals;

transmitting said digitized signals in a serial stream to a processing system.

3. The method of noninvasively detecting cerebral irregularities of claim 1 wherein said step of computing bispectral values comprises:

computing a fast Fourier transform for each of said records of said acquired signals;

computing a power spectrum for each of said data records;

computing individual complex triple product arrays for each of said records of said acquired signals and then computing an average complex triple product array of all of said individual complex triple product arrays;

computing individual real triple product arrays for each of said records of acquired signals and then computing an average real triple product array of all said individual real triple arrays;

computing a bispectral density array.

4. The method of noninvasively detecting cerebral irregularities of claim 3 wherein said complex triple product array, represented by $bc_i(f_1,f_2)$, for each data record, represented by $x_i(t)$, where $0 \leq i \leq y$ is computed as follows:

$$bc_i(f_1,f_2) = X_i(f_1) * X_i(f_2) * \overline{X_i(f_1+f_2)}$$

$$f_1 + f_2 \leq N/2$$

$$0 \leq f_2 \leq f_1$$

where $X_i(f)$ is the fast Fourier transform of a record.

5. The method of noninvasively detecting cerebral irregularities of claim 3 wherein the average complex triple product array, represented by $BC(f_1, f_2)$, of the individual triple product arrays, represented by $bc_i(f_1, f_2)$, is computed as follows:

$$BC(f_1, f_2) = 1/y \left[ \sum_{i=1}^{y} bc_i(f_1, f_2) \right].$$

6. The method of noninvasively detecting cerebral irregularities of claim 3 wherein said real triple product array, represented by $bc_i(f_1, f_2)$, for each data record, represented by $x_i(t)$, where $0 \leq i \leq y$ is computed as follows:

$$br_i(f_1, f_2) = X_i(f_1) * X_i(f_2) * \overline{X_i(f_1 + f_2)}$$

$$f_1 + f_2 \leq N/2$$

$$0 \leq f_2 \leq f_1$$

where $X_i(f)$ is the fast Fourier transform of a record.

7. The method of noninvasively detecting cerebral irregularities of claim 3 wherein the average real triple product array, represented by $BR(f_1, f_2)$, of the individual triple product arrays, represented by $br_i(f_1, f_2)$, is computed as follows:

$$BR(f_1, f_2) = 1/y \left[ \sum_{i=i}^{y} br_i(f_1, f_2) \right]$$

8. The method of noninvasively detecting cerebral irregularities of claim 3 wherein said bispectral density array, represented by $BD(f_1, f_2)$, is computed as follows:

$$BD(f_1, f_2) = |BC(f_1, f_2)|^2$$

Where $BC(f_1, f_2)$ represents said average complex triple array.

9. The method of noninvasively detecting cerebral irregularities of claim 3 further comprising the step of computing a bicoherence array.

10. The method of noninvasively detecting cerebral irregularities of claim 9 wherein said step of computing the bicoherence array represented by $R^2(f_1, f_2)$ comprises the step of calculating:

$$R^2(f_1, f_2) = BD(f_1, f_2) / BR(f_1, f_2)$$

$$0 \leq R^2 \leq 1$$

where
$BD(f_1, f_2)$ represents said bispectral density array, and $BR(f_1, f_2)$ represents said average real triple product array.

11. The method of noninvasively detecting cerebral irregularities of claim 1 wherein said step of utilizing said bispectral values to quantify the contribution to overall cerebral electrophysiologic activity provided by the region probed by said surface electrode comprises the step of:
  determining the depth of anesthesia by producing indexes representing the sum of all absolute values of the changes in each element in an array of bispectral values, said indexes gradually increasing during the induction of anesthesia until a maximum is reached when the anesthesia takes full effect.

12. The method of noninvasively detecting cerebral irregularities of claim 1 wherein said step of utilizing said bispectral values to quantify the contribution to overall cerebral electrophysiologic activity provided by the region probed by said surface electrode comprises the step of determining the depth of anesthesia and said step of determining the depth of anesthesia, comprises the steps of:
  producing a bispectral density array and a bicoherence array from the signals received through each of said electrodes;
  subtracting said bispectral density array of each electrode from a preanesthesia control bispectral array of that electrode;
  computing a bispectral density index for each lead representing the sum of all of the absolute values of the changes in each element in said bispectral density array;
  subtracting said bicoherence array of each electrode from a preanesthesia control bicoherence array of that electrode;
  computing a bicoherence index for each lead representing the sum of all the absolute values of the changes in each element in said bicoherence array;
  said indexes gradually increasing during the induction of anesthesia until a maximum is reached when the anesthesia takes full effect.

13. The method of noninvasively detecting cerebral irregularities of claim 12 further comprising the step of:
  displaying said bispectral density index and said bicoherence index on a grid, said grid having an area representing a location of each electrode on the surface of the skull with each area containing both the bispectral density index and the bicoherence index.

14. The method of noninvasively detecting cerebral irregularities of claim 1 wherein said step of utilizing said bispectral values to quantify the contribution to overall cerebral electrophysiologic activity provided by the region probed by said surface electrode comprises the step of determining the depth of anesthesia, said step of determining the depth of anesthesia comprises the steps of:
  producing a bispectral density array of the signals received through each of said electrodes;
  correlating said bispectral density array with a control spectral density array in order to produce a cross-correlation coefficient, said cross-correlation coefficient gradually decreasing during the induction of anesthesia until a minimum is reached when the anesthesia takes full effect.

15. The method of noninvasively detecting cerebral irregularities of claim 14 further comprising the step of:
  displaying the cross-correlation coefficient of the bispectral density array on a grid, said grid having an area representing a location of each electrode on the surface of the skull with each area displaying a numerical representation of the cross-correlation coefficient of the bispectral density array.

16. The method of noninvasively detecting cerebral irregularities of claim 1 wherein said step of utilizing said bispectral values to quantify the contribution to overall cerebral electrophysiologic activity provided by the region probed by said surface electrode comprises the step of determining the depth of anesthesia, said step of determining the depth of anesthesia comprises the steps of:
  producing a bicoherence array of the signals received through each of said electrodes;

correlating a bicoherence array with a control bicoherence array in order to produce a cross-correlation coefficient, said cross-correlation coefficient gradually decreasing during the induction of anesthesia until a minimum is reached when the anesthesia takes full effect.

17. The method of noninvasively detecting cerebral irregularities of claim 16 further comprising the step of:
displaying the cross-correlation coefficient of the bicoherence array on a grid, said grid having an area representing a location of each electrode on the surface of the skull with each area displaying a numerical representation of the cross-correlation coefficient of the bicoherence array.

18. The method of noninvasively detecting cerebral irregularities of claim 1 wherein said step of utilizing said bispectral values to quantify the contribution to overall cerebral electrophysiologic activity provided by the region probed by said surface electrode determines a degree of intoxication due to the use of alcohol or drugs.

19. The method of noninvasively detecting cerebral irregularities of claim 1 wherein said step of utilizing said bispectral values to quantify the contribution to overall cerebral electrophysiologic activity provided by the region probed by said surface electrode determines adequacy of oxygenation of a cortical region probed by a particular electrode.

20. The method of noninvasively detecting cerebral irregularities of claim 1 wherein said step of utilizing said bispectral values to quantify the contribution to overall cerebral electrophysiologic activity provided by the region probed by said surface electrode determines a cortical area affected by ischemia.

21. A system for noninvasively detecting cerebral irregularities that affect cerebral electrical acitvity, said system comprising:
means for acquiring electroencephalographic signals from a surface of the head of a subject being analyzed;
means for dividing said acquired electroencephalographic signals into a plurality of data records;
means for computing at least one array of bispectral values from said data records of electroencephalographic signals;
means for utilizing said at least one array of bispectral values to generate single number indices to quantify a contribution to overall cerebral electrophysiologic stability provided by a region to which said means for acquiring electroencephalographic signals is connected.

22. The system for noninvasively detecting cerebral irregularities of claim 21 wherein said means for acquiring electroencephalographic signals is a plurality of electrodes adapted to be attached to said surface of the head of the subject being analyzed.

23. The system for noninvasively detecting cerebral irregularities of claim 21 wherein said means for acquiring electroencephalographic signals comprises a surface electrode adapted to be attached to the head of the subject being analyzed.

24. The system for noninvasively detecting cerebral irregularities of claim 21 wherein said means for acquiring electroencephalographic signals comprises:
a plurality of surface electrodes mounted on said surface of the head of the subject being analyzed;
means for providing electrosurgery protection including a radio frequency filter for limiting radio frequency current to said electrodes;
means for providing defibrillator protection for limiting the current through said electrodes during a defibrillator discharge;
means for amplifying signals acquired by said electrodes;
means for multiplexing said amplified signals so as to provide one signal at a time in a serial stream, said signal being fed to a means for converting analog signals into digital signals in order to convert said amplified signals into digital signals.

25. The system for noninvasively detecting cerebral irregularities of claim 21 wherein said means for computing at least one array of bispectral values comprises a computer system including:
means for receiving data in a serial stream from said means for acquiring electroencephalographic signals;
an array processor for performing arithmetic calculations on an entire array of data simultaneously;
a math coprocessor for calculating graphic modalities;
means for controlling receipt of input data or other signals from peripheral devices connected to said means for computing and means for controlling output of data or other signals to peripheral devices connected to said means for computing.

26. The system for noninvasively detecting cerebral irregularities of claim 21 wherein said cerebral irregularities being detected is a depth of anesthesia.

27. The system for noninvasively detecting cerebral irregularities of claim 21 wherein said cerebral irregularities is a degree of intoxication due to alcohol or drugs.

28. The system for noninvasively detecting cerebral irregularities of claim 21 wherein said system determines a cortical area effected by ischemia.

* * * * *